(12) United States Patent
Haas et al.

(10) Patent No.: US 9,188,510 B2
(45) Date of Patent: Nov. 17, 2015

(54) TEST SWIPE FOR PORTABLE EXPLOSIVE OR DRUG DETECTION SYSTEM

(71) Applicants: Jeffrey Haas, San Ramon, CA (US); Douglas Haas, Lancaster, CA (US)

(72) Inventors: Jeffrey Haas, San Ramon, CA (US); Douglas Haas, Lancaster, CA (US)

(73) Assignee: CHEMSPECTRA, INC., Lancaster, CA (US)

( * ) Notice: Subject to any disclaimer, the term of this patent is extended or adjusted under 35 U.S.C. 154(b) by 635 days.

(21) Appl. No.: 13/623,877

(22) Filed: Sep. 21, 2012

(65) Prior Publication Data

US 2015/0260741 A1    Sep. 17, 2015

Related U.S. Application Data

(63) Continuation of application No. 12/393,427, filed on Feb. 26, 2009, now abandoned.

(51) Int. Cl.

| | |
|---|---|
| *G01N 21/75* | (2006.01) |
| *G01N 1/02* | (2006.01) |
| *G01N 35/00* | (2006.01) |
| *G01N 21/78* | (2006.01) |
| *G01N 25/00* | (2006.01) |
| *G01N 33/22* | (2006.01) |
| *G01N 33/94* | (2006.01) |

(52) U.S. Cl.
CPC .................. *G01N 1/02* (2013.01); *G01N 21/78* (2013.01); *G01N 25/00* (2013.01); *G01N 33/227* (2013.01); *G01N 33/94* (2013.01); *G01N 35/00009* (2013.01); *G01N 35/00722* (2013.01); *G01N 2001/022* (2013.01); *G01N 2001/028* (2013.01); *G01N 2035/0091* (2013.01); *G01N 2035/0097* (2013.01); *G01N 2035/00425* (2013.01); *G01N 2201/0231* (2013.01); *Y10T 436/25375* (2015.01)

(58) Field of Classification Search
CPC .................. G01N 35/00009; G01N 33/0091; G01N 33/227; G01N 33/22; G01N 33/94; G01N 1/02; G01N 1/44; G01N 2001/022; G01N 2001/024; G01N 2001/025; G01N 2001/027; G01N 2001/028; Y10T 436/25375; Y10T 436/25

See application file for complete search history.

(56) References Cited

U.S. PATENT DOCUMENTS

| | | | | |
|---|---|---|---|---|
| 4,250,257 | A | * | 2/1981 | Lee et al. ........................... 435/4 |
| 5,408,535 | A | * | 4/1995 | Howard et al. ................ 382/128 |
| 5,508,200 | A | * | 4/1996 | Tiffany ................ B01J 19/0046 422/66 |
| 5,648,047 | A | * | 7/1997 | Kardish et al. ................. 422/411 |
| 6,518,068 | B1 | * | 2/2003 | Gambini et al. ................. 436/50 |
| 2004/0265169 | A1 | * | 12/2004 | Haas et al. ....................... 422/56 |
| 2009/0246881 | A1 | * | 10/2009 | Toal et al. ...................... 436/110 |

OTHER PUBLICATIONS

Manual for Spectrex EX—Detect M, Model XD-2 Explosives Detector, Mar. 2007.*
Chen Zhang et al. "Colorimetric sensor arrays for the analysis of beers: A feasibility study." J. Agric. Food Chem. (2006) 54 4925-4931.*

* cited by examiner

*Primary Examiner* — Christopher A Hixson
(74) *Attorney, Agent, or Firm* — Tran & Associates

(57) ABSTRACT

A portable chemical analytical apparatus to analyze a test swipe having a base; a chemically treated pad containing the swiped sample positioned in a white zone above the base; and a tab attached to one side of the base. The apparatus includes a heater to warm the test swipe to a predetermined temperature; a clamp to secure the test swipe to the heater; one or more pumps to dispense one or more chemicals onto the test swipe from a disposable cartridge; a fan to remove chemical vapors rising a predetermined distance from the test swipe; and a camera to capture an image of the test swipe for un-biased automated analysis, and displayed on an LCD screen.

19 Claims, 16 Drawing Sheets

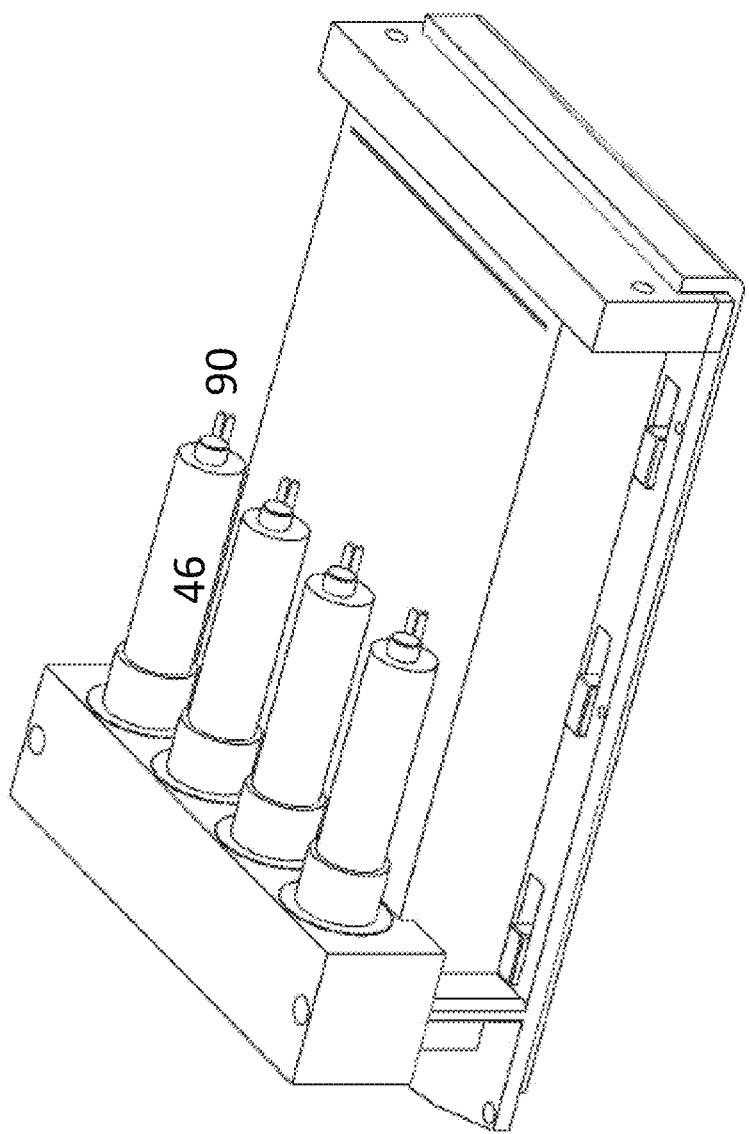

TEST SWIPE FOR PORTABLE EXPLOSIVE OR DRUG DETECTION SYSTEM

This application is a continuation of U.S. application Ser. No. 12/393,427, filed Feb. 26, 2009, the content of which is incorporated by reference.

BACKGROUND

This invention relates to systems for the detection of explosives and other controlled substances such as drugs or narcotics as well as other chemicals used in clandestine activities.

Recent terror attacks have changed the dynamics of the explosive detection systems across the globe. Terrorists, acting singly or in concert, instill immense fear and apprehension in civilians and governments alike with their technical knowledge about explosives. In parallel, the world has experienced an increase in the transportation of contraband substances such as drugs or narcotics.

With advances in explosives technology, such as the advent of the plastic explosives, which can be disguised as common items, it is becoming increasingly difficult to detect these substances. The problems that must be overcome in the detection of these substances as well as others, include low vapor pressure of the particular vapors escaping from the particular substance, the search time and the throughput of the various systems, the low concentration of vapor or particulate emissions from the particular substance, isolation of the particular substance with a high degree of reliability, and maintaining the integrity of the systems environment.

Various techniques for detecting substances such as explosives and drugs or narcotics have been developed, ranging from explosives/drug sniffing dogs to highly sophisticated vapor detection devices. Machine detection of the aforementioned substances can be accomplished through non-vapor detection or vapor detection. Non-vapor detection methods include x-ray detection, gamma-ray detection, neutron activation detection and nuclear magnetic resonance detection. These methods of detection are more applicable to the detection of the various substances when the substances are concealed and are carried or associated with non-living items such as baggage as these techniques might pose a threat to living items. Vapor detection methods include electron capture detection, gas chromatography detection, mass spectroscopy detection, plasma chromatography detection, bio-sensor detection and laser photo-acoustic detection. These methods of detection are more applicable to the detection of substances that are concealed and associated with living specimens.

Conventional systems tend to be large and immobile. Further, current systems can require users to manually apply toxic chemicals as testing agents. As a result, conventional systems are not mobile and hard to use. Hence, their adoption for field use has been limited.

SUMMARY

In one aspect, a test swipe includes a base; a chemically treated pad positioned above the base; and a tab attached to one side of the base.

Implementations of the above aspect may include one or more of the following. The chemically treated pad can be a substantially round shape. A sequence of one or more chemicals can be delivered to the pad to detect an explosive compound. Each chemical causes the pad to display a color unique to the explosive compound. The sequence of chemicals are deposited onto the pad at predetermined times. The sequence of chemicals is deposited onto the pad at predetermined temperature range(s). The sequence of chemicals is deposited onto the pad at predetermined hold time(s) each at predetermined temperature range(s). Each chemical deposited under predetermined time and temperature conditions reacts to a specific explosive or class of explosives to yield a specific color unique to that explosive. The color is interpreted by the algorithms at specific times, temperature and chemistry to identify or characterize the explosive or class of explosives. The chemically treated pad can be a substantially round shape and adapted to receive a sequence of one or more chemicals to detect an explosive compound. The base can have a dull black color. The pad region can be a cloth with an ink free border.

The chemically treated pad can also be a substantially four-sided shape. One or more chemicals can be deposited onto their respective pads to detect one or more drug compounds. Each chemical causes the pad to display a color unique to the explosive compound. The sequence of chemicals are deposited onto their respective pads at predetermined times. The sequence of chemicals are deposited onto the pad at predetermined temperature range(s). The sequence of chemicals are deposited onto the pad at predetermined hold time(s) each at predetermined temperature range(s). Each chemical deposited under predetermined time and temperature conditions reacts to a specific explosive or class of explosives to yield a specific color unique to that explosive. The chemically treated pad can be a substantially four-sided shape and adapted to receive a sequence of one or more chemicals to detect a drug compound. The chemically treated area can have a plurality of test regions. A plurality of unique chemical solutions can be deposited on each test region generating a unique color of the respective pad. The pads collectively generate a unique color pattern or code for a particular drug or class of drugs. The chemical solutions can be deposited separately or at same time to the respective test regions on the swipe. The base can have a dull black color. The pad region can be a cloth positioned on a zone of the base that is white in color an inert ink free border.

In another aspect, a method to analyze a swiped sample to identify a chemical composition, includes clamping a test swipe under a camera and above a heater, the test swipe having a base; a chemically treated pad containing the swiped sample positioned above the base; and a tab attached to one side of the base; automatically pumping a series of chemical solution agents into the swiped sample without dripping so that the device may be held at any angle of position or orientation; heating the swiped sample to one or more predetermined temperatures at a controlled rate and hold times to optimize and accelerate the chemical reactions; capturing one or more images of the chemical reaction; sending the images to the a display screen for operator observation; and analyzing the images to identify the chemical composition based on a chemical reaction and sequence of occurrence and database.

In yet another aspect, a portable handheld chemical analytical apparatus to analyze a test swipe for chemicals such as household, drug, and clandestine, and explosive chemicals is disclosed. The apparatus includes a heater to warm the test swipe to a predetermined temperature; a clamp to secure the test swipe to the heater; one or more pumps to dispense one or more chemicals onto the test swipe; a fan to circulate chemical vapors rising from the test swipe; and a camera to capture an image of the test swipe for analysis.

In another aspect, a method to analyze a swiped sample to identify a chemical composition, includes automatically pumping a series of chemical solution agents into the swiped sample; heating the swiped sample to one or more predetermined temperatures at a controlled rate to accelerate and optimize the chemical reactions or a series of chemical reactions reproducibly; capturing one or more images of the chemical reaction; sending the images to the a display screen for operator observation; and analyzing the images electronically to identify the chemical composition in an unbiased fashion based on a chemical reaction database.

Advantages of the system may include one or more of the following. The system tests the presence of chemical materials or compounds using a number of factors or parameters singly or in concert. The factors can include heat, volume, time, temperature, and vapor control, among others and sequences these factors over time. The sequences can be in unique intervals. As a result, the system is highly reliable color results from specific reaction chemistry under the controlled parameters and reduces "false positives" due to its multi-factor, multi-step diagnostic operations.

The system significantly enhances the possibility of accurately and quickly screening personnel, equipment, and materials at security checkpoints, military operations, law enforcement, or other screening scenarios, and for detecting trace explosive materials, night or day, very high humidity and bad-weather conditions. The system allows users to precisely and quickly detect different explosive chemical agents.

The system operates in a real-time fashion. It automatically dispenses a precise volume of chemical solutions over time when requested. The system optionally allows users to manually control the sequence of the pumping process. The system provides users with pump controls for dispensing chemical solutions. Through the built-in heater, the system automatically heats up the swiped sample to predetermined temperatures over specific time parameters using an automatic ramped heating feedback control. The system automatically and continually performs self-check and monitors fluid levels, temperature and time. The system automatically chronologically stores data and arranges according to positive results versus negative results. The system automatically tells the operator to remove the analyzed swipe. The system delivers a unique sequence of precise chemical volumes under time, heat, and vapor parameters. The system has detachable and expendable chemical(s) in cartridge form for ease of replacement. The system uses a high-resolution digital camera for data collection and un-biased automated analysis.

By use of a wired or wireless transceiver, detected information can be easily transmitted to anywhere in the world. By replacing disposable swipes/pads/swabs and disposable chemical test reservoirs, the system can detect a wide range of explosives, clandestine material, drugs, and household products used to manufacture explosives, a range of controlled chemical agents, drugs, and narcotics etc. By allowing the user to swipe test materials and running computerized diagnostics, the user can easily and effectively change the system to meet what is considered to be the threat at that time. By having all components under program control and by arranging for a known input to the system such as a controlled injection of target material, the system can perform self-calibration and self-diagnostics.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which:

FIG. 2A shows an exemplary portable chemical detection device, while

FIG. 4C shows an exemplary perspective view of a micropump array.

DESCRIPTION

The following detailed description of the invention is provided to aid those skilled in the art in practicing the present invention. Even so, the following detailed description of the invention should not be construed to unduly limit the present invention, as modifications and variations in the embodiments herein discussed may be made by those of ordinary skill in the art without departing from the spirit or scope of the present inventive discovery.

Figure 1A:
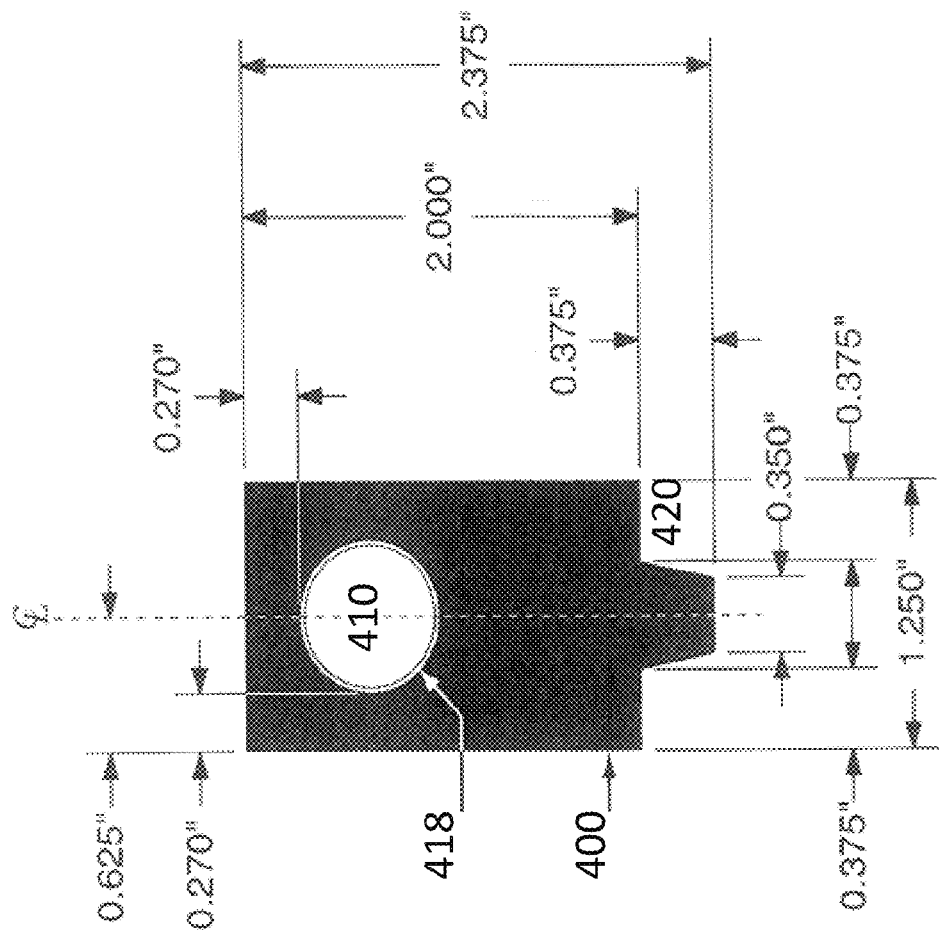
FIG. 1A shows a first embodiment of a test swipe.

FIG. 1A shows a test swipe with a base 400, a chemically treated pad positioned above the base 410; and a tab 420 attached to one side of the base 400. In the embodiment of FIG. 1A, the chemically treated pad has a substantially round shape. A sequence of one or more chemicals can be delivered to the pad to detect an explosive compound. Each chemical or chemical sequence in tandem with temperature parameters over time causes the pad to display a color unique to the explosive compound. The sequence of chemicals are deposited onto the pad at predetermined times. The sequence of chemicals is deposited onto the pad at predetermined temperature range(s) achieved at a specific ramp rate. The sequence of chemicals is deposited onto the pad at predetermined hold time(s) each at predetermined temperature range(s). Each chemical deposited under predetermined time and temperature conditions reacts to a specific explosive or class of explosives to yield a specific color unique to that explosive. The chemically treated pad can be a substantially round shape of thickness less than 0.005 inches to achieve rapid, and even heating through the material layer, and adapted to receive a sequence of one or more chemicals to detect an explosive compounds. The base 400 can have a non reflective dull black color. The pad region 418 can be a cloth within a white zone on the base and an ink free border.

The round swipe of FIG. 1A can be used for explosives in which a sequence of unique chemicals are deposited onto the same circular pad at specified times, temperature ramp rates, and hold times at a given temperature. Each chemical deposited under these time/temp conditions will react a specific explosive or class of explosives yielding a specific color unique to that explosive or class of explosives.

Figure 1B:
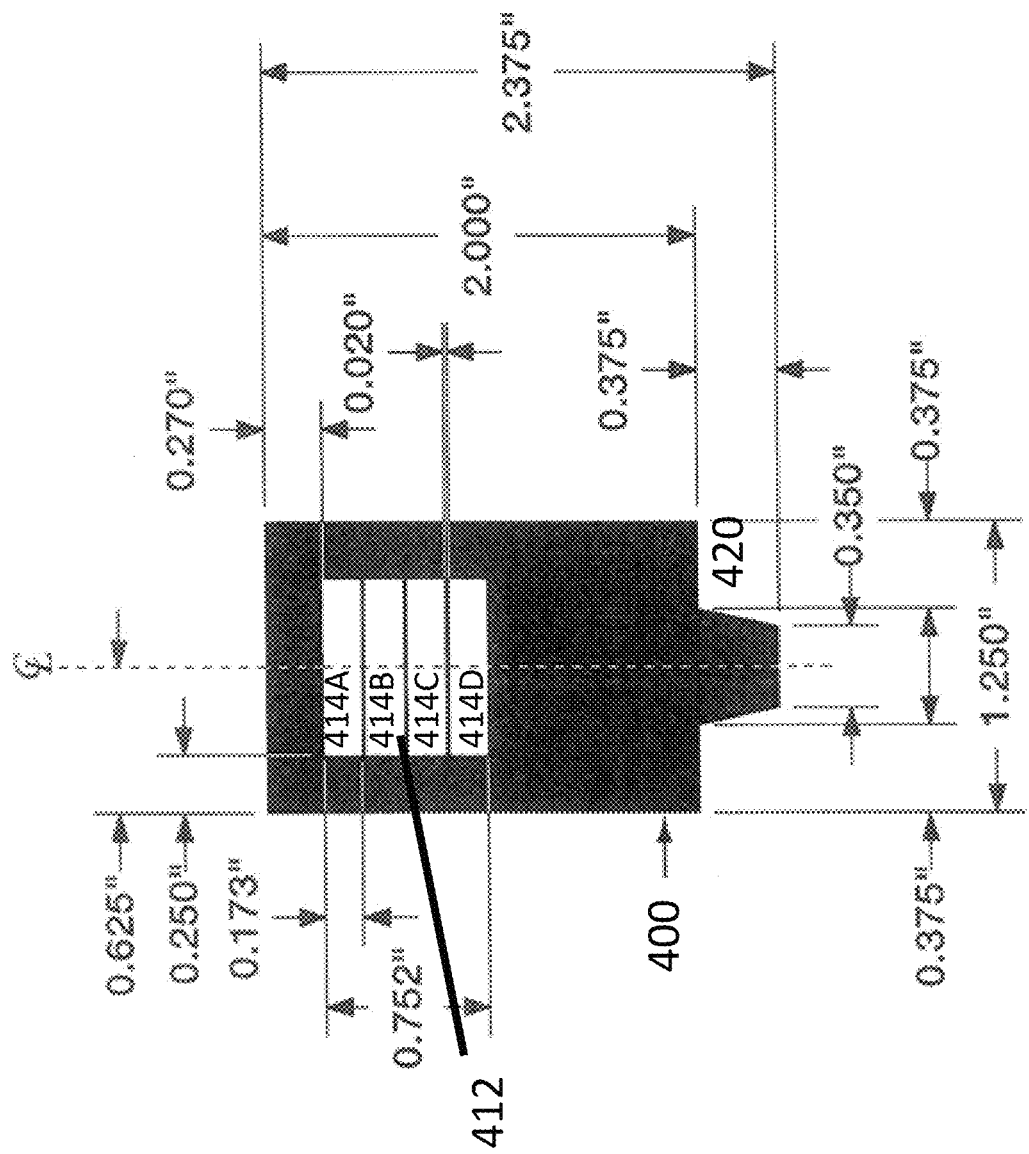
FIG. 1B shows a second embodiment of the test swipe.

Turning now to FIG. 1B, a chemically treated pad 412 can be a substantially four-sided shape. The chemically treated area 412 can have a plurality of test regions 414A-414D. A plurality of unique chemical solutions can be deposited on each test region. The chemical solutions can be deposited separately or at same time to the respective test regions on the swipe. One or more chemicals can be deposited onto the pad to detect one or more drug compounds. Each chemical causes the pad to display a color unique to the explosive compound or class of explosives. The colors generated on each pad, in combination, subsequently generate a color bar code unique to the drug or class of drugs. The sequence of chemicals are deposited onto the pad at predetermined times. The sequence of chemicals are deposited onto the pad at predetermined temperature range(s). The sequence of chemicals are deposited onto the pad at predetermined hold time(s) each at predetermined temperature range(s). Each chemical deposited under predetermined time and temperature conditions reacts to a specific explosive or class of explosives, drug or class of drugs to yield a specific color unique to that explosive or drug. The chemically treated pad can be a substantially four-sided shape of thickness less than 0.005 inches to achieve rapid and even heating through the material layer, and adapted to receive a sequence of one or more chemicals to detect a drug compound.

The drug swipe embodiment of FIG. 1B can have four different solutions deposited at same time to the respective rectangles on the swipe. The portable test device (FIG. 2A) will read the "color bar code" results to determine certain drugs. Then, the swipe will be heated through one to several heat ramp cycles to invoke more color changes to each of the respective rectangles creating new color bar codes. Each color bar code at a specific temperature and time will indicate a specific drug or clandestine material sought. A sampler/applicator can be used to sample a suspect material; in a baggie for example; and wipes the collected drug sample onto the square swipe pad (made up of four rectangles 414A-414D).

The swipe pad may be formed of material that may be resistant to chemical degradation during testing in the approximate pH range of 0.1 through 14 to avoid reacting or decomposing. The swipe pad may be white in color to aid test evaluation, may be heat resistant and chemically resistant at elevated temperatures up to approximately 150° C. and may have hydrophilic properties for wetting only when using fluid reagents in the test apparatus. The swipe pad may also be roughened, for example, by use of a woven material, to aid in retrieving test sample particles from the environment. The swipe pad may also be thick enough to resist damage such as tearing during sampling, yet not be too thick such that heating of the test sample is inhibited. A thickness less than 0.005 inches to achieve rapid, and even heating through the material layer.

The test swipe can be used to swipe a sample to identify a chemical composition. This can be done by clamping the test swipe under a camera and above a heater, the test swipe having a base; a chemically treated pad containing the swiped sample positioned above the base in a white zone; and a tab attached to one side of the base; automatically pumping a series of chemical solution agents into the swiped sample without dripping so that the device may be held in any orientation; heating the swiped sample to one or more accurate predetermined temperatures and hold times to optimize and accelerate the chemical reactions; evacuation of vapors generated, capturing one or more images of the chemical reaction; sending the images to the a display screen for operator observation; and analyzing the images to identify the chemical composition based on a chemical reaction and sequence of occurrence and database.

The chemical solution agents are described next. A Tetrabutylammonium hydroxide formulation may be used in a reagent test to impart a color to nitroaromatic compounds that may otherwise not be detected by other bases, such as, sodium hydroxide or potassium hydroxide regardless of their respective concentrations. The tetrabutylammonium hydroxide may also be strong enough to create nitrite salts for other types of explosives that may be in the test sample in preparation for testing with a second type reagent. Use of tetrabutylammonium hydroxide may be difficult due to limited shelf life and its reaction to environmental carbon dioxide that may degrade the necessary color chemistry with nitroaromatics. To develop a solvent system mixable with water to inhibit degradation and reduce hazardous effects to a user, an ethanol and water mixture may be used to inhibit tetrabutylammonium hydroxide degradation with the ethanol ratio such as not to be flammable. The ethanol and water may also have minimum nitrite content to avoid reaction to a second type reagent test that may give false positive results. The tetrabutylammonium hydroxide may also be of a concentration in the ethanol water mixture so as not to interfere chemically with subsequent formulations added to the swipe. For example, if a 10 nanogram detection threshold may be used, any nitrite content in the solutions may be less than 0.2 nanograms per microliter of fluid to minimize corruption of test results or false detection.

The first reagent test may use a first reagent fluid that may have an optimum detection performance range with the fluid having a tetrabutylammonium hydroxide in a water solution in the approximate range of 65-850 percent and an ethanol as approximately 20-35 percent of the water solution. Test results may be obtained using a wider tolerance of elements in the first reagent fluid, but there may be reduced detection sensitively. The tetrabutylammonium hydroxide in water solution may be in the approximate range of 0.1 to 1.6 Molar and the ethanol as approximately 5 to 95 percent of the water solution. Also, other alcohols or blends of alcohols may be used in place of ethanol; however, for example, methanol may be toxic to the user and isopropyl may be less toxic, but may have poorer detection sensitivity results and cause shorter shelf life for the reagent fluid.

A second reagent test may be a Griess reagent test. The Griess reagent may cause a highly colored azo dye to be created in a reaction with nitrite salts generated from the first reaction or present as residue from firearms. The acid that may be used in the formulation of the second reagent may be phosphoric acid that reduces hazardous effects to a user that may become a buffer during the reaction thereby buffering against itself to inhibit creation of too much acid on the swipe pad 42. Other types of acids that may be used in the Griess test may react too violently with other bases, may be toxic or hazardous, or may create a strong odor.

The phosphoric acid may be mixed with sulfanilic acid and N-(1-naphthyl) ethylenediamine dihydrochloride. The sulfanilic acid may be water soluble with reduced toxicity in combination with and it may impart a deep magenta or fuchsia color to the test sample for ease of detection of explosives. N-(1-naphthyl) ethylenediamine dihydrochloride may be water soluble and not carcinogenic as with other salts, and may impart an effective color reaction from the test sample. The second reagent solution may use deionized water that may have minimum nitrite content to reduce false positive test results. For example, if a 10 nanogram detection threshold may be used any nitrite content in the solutions may be less than 0.2 nanograms per microliter of fluid to minimize corruption of test results or false detection.

The second reagent test may use a second reagent fluid that may have an optimum detection performance range with the fluid having a phosphoric acid in a water solution in the approximate range of 1.3 to 1.7 Molar; and a sulfanilic acid of approximately 8 grams with a N-(1-naphthyl) ethylenediamine dihydrochloride of approximately 5 grams per 1000 milliliters of the phosphoric acid in water solution. Test results may be obtained using a wider tolerance of elements in the second reagent fluid, but there may be reduced detection sensitivity. The phosphoric acid in water solution may be in the approximate range of 0.1 to 7.35 Molar, the sulfanilic acid may be in the approximate range of 5 to 8 grams, and the N-(1-naphthyl) ethylenediamine dihydrochloride may be in the approximate range of 5 to 9 grams. Other acids, acid combinations, or acid concentrations may be used, but may produce less than optimal testing sensitivity results. Other solutions may have increased acidity and be hazardous to the user as well as have a detrimental effect on the testing device. Other solutions may not be acidic enough for a detection reaction to occur or may be toxic. Other salts may be used, but they may reduce the explosives detection sensitivity.

Figure 2A:
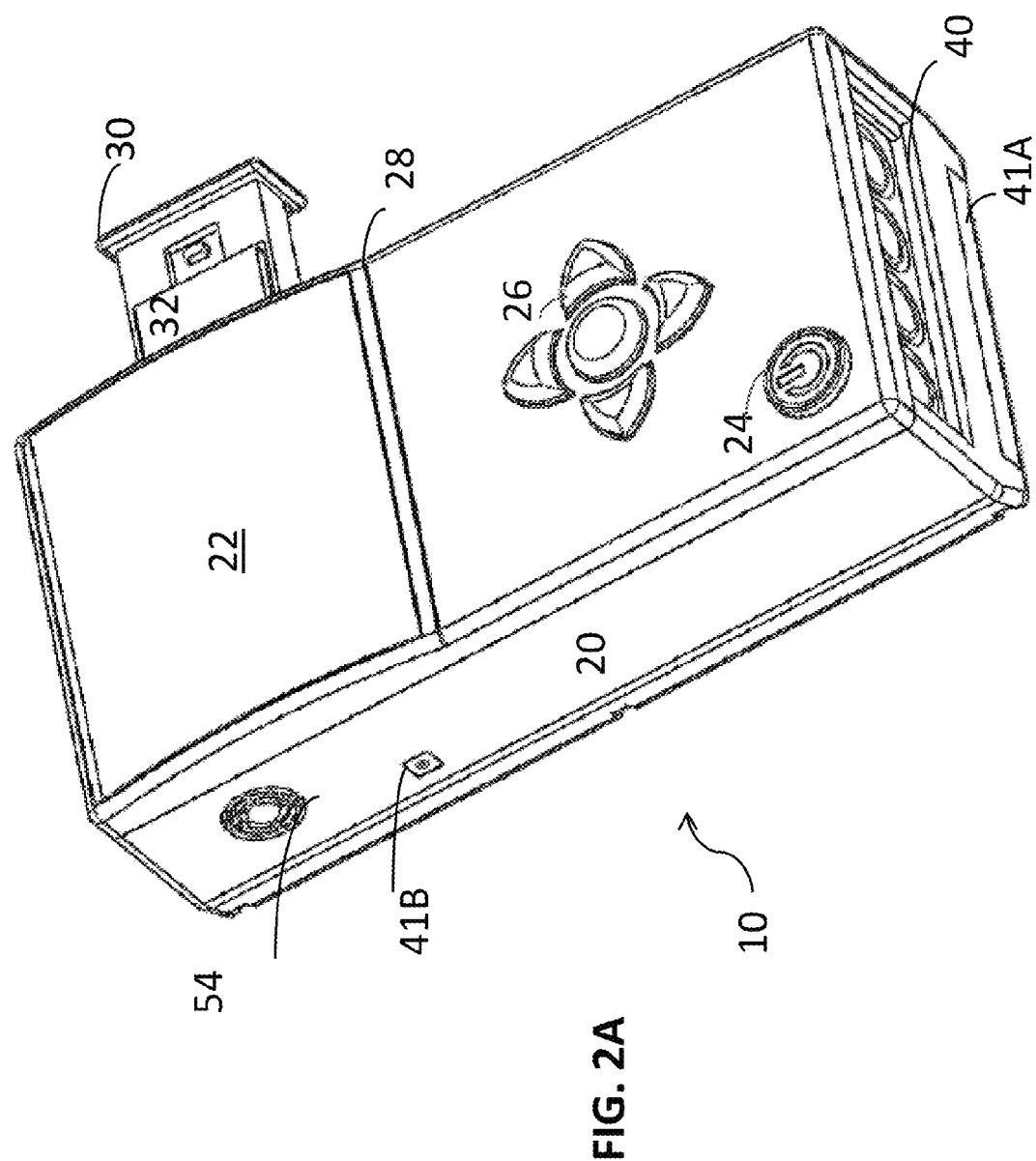

FIG. 2A shows an exemplary portable chemical detection device 10 that uses the test swipe of FIG. 1A or 1B. The device 10 has a housing 20 that supports a display 22 and input devices such as an on-off button 24 and navigation/selection buttons 26. In one embodiment, the system has six buttons. The first button is the On/Off button. This button allows user to turn the unit on or off. The remaining five buttons (Left, Right, Down, Up, and Enter) allows user to interact with a Graphical User Interface (GUI) of the system. The GUI is flexible, efficient and user friendly.

The device 10 also has an input/output port 28 such as a USB port or Firewire port to communicate with a remote computer, and AC power port, among others. In one embodiment, the I/O port 28 is a weather proof PC interface. The PC interface can set up operation parameters and recover analyzed data. In another embodiment, the I/O port 28 can include a flash memory card interface.

The device 10 also includes two ports 30 and 40 to receive user replaceable media and chemical. The device 10 also includes a port 41A to receive user replaceable DC battery cartridge. Port 30 receives a test swipe of FIGS. 1A and 1B. The port 40 receives a chemical cartridge, which can house one or more chemical containers. An electronic controller 58 (shown in FIGS. 2A AND 2B) receives inputs from the buttons or keys and controls the display 22 and other electronics in the device 10. The system can work with different power sources including battery port 41A port and/or a DC input port 41B such as a car jack or an AC/DC adaptor.

The system of FIG. 2A is preferably a hand-held unit, which can most preferably be operated easily in real time by one operator. Moreover, the operation of such detectors should preferably be simple so that non-technical persons can operate the instrument properly, efficiently, and easily.

Figure 2B:
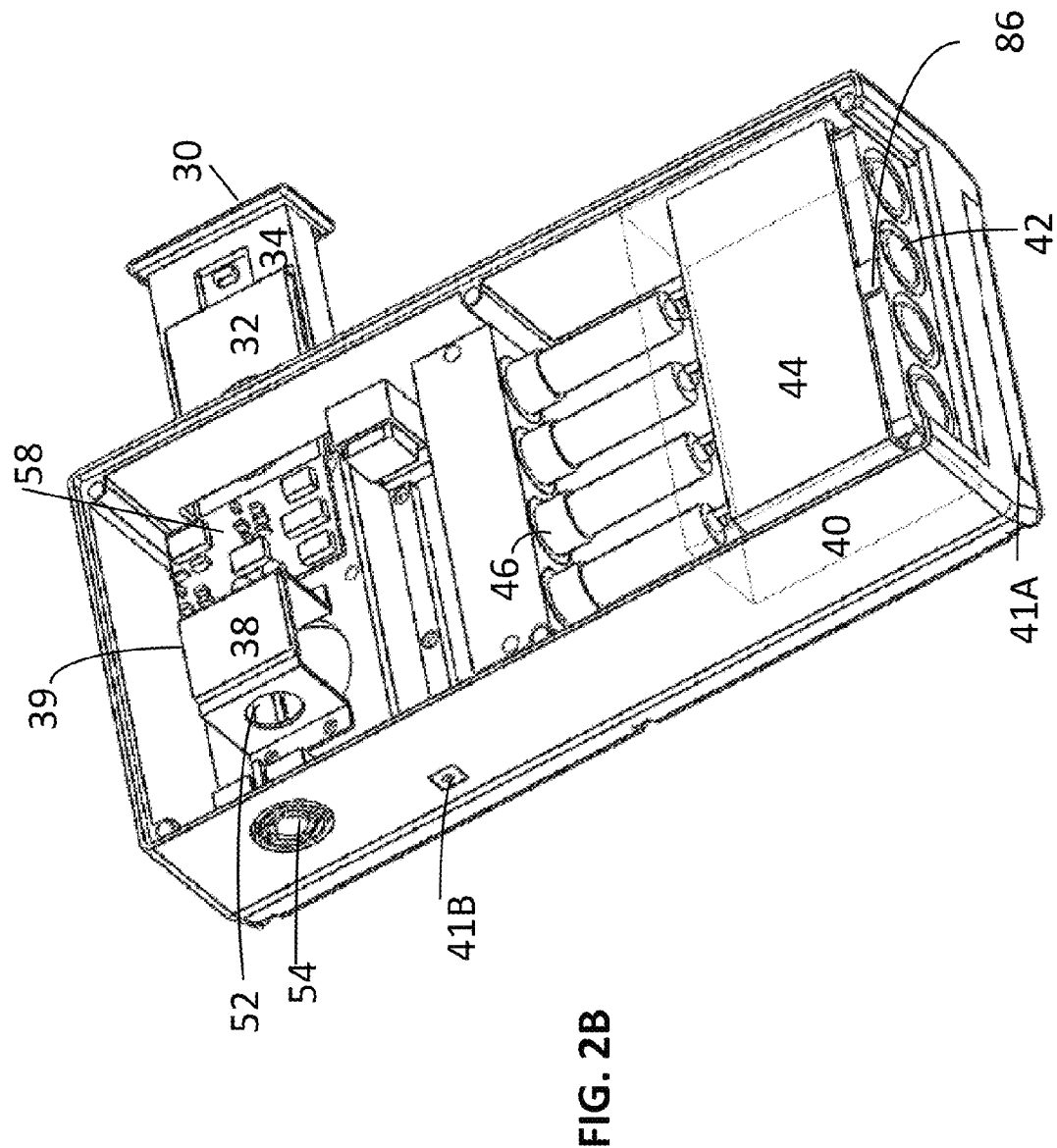
FIG. 2B shows in more details major components of the device.

FIG. 2B shows a perspective top view that show in more details major components of the device 10. In the embodiment of FIG. 2B, a plurality of chemical containers or reservoirs 42 are mounted in a disposable cartridge 44 that is inserted into the unit 10. The reservoirs 42 are punctured via safety needles with a side port and the chemicals are automatically or manually pumped from the reservoirs 42 by one or more micro-pumps 46. The chemicals are delivered through one or more short length and narrow ID delivery tubes connected to the outputs of the micro-pumps 46 to the test swipe during testing.

Figure 5A:
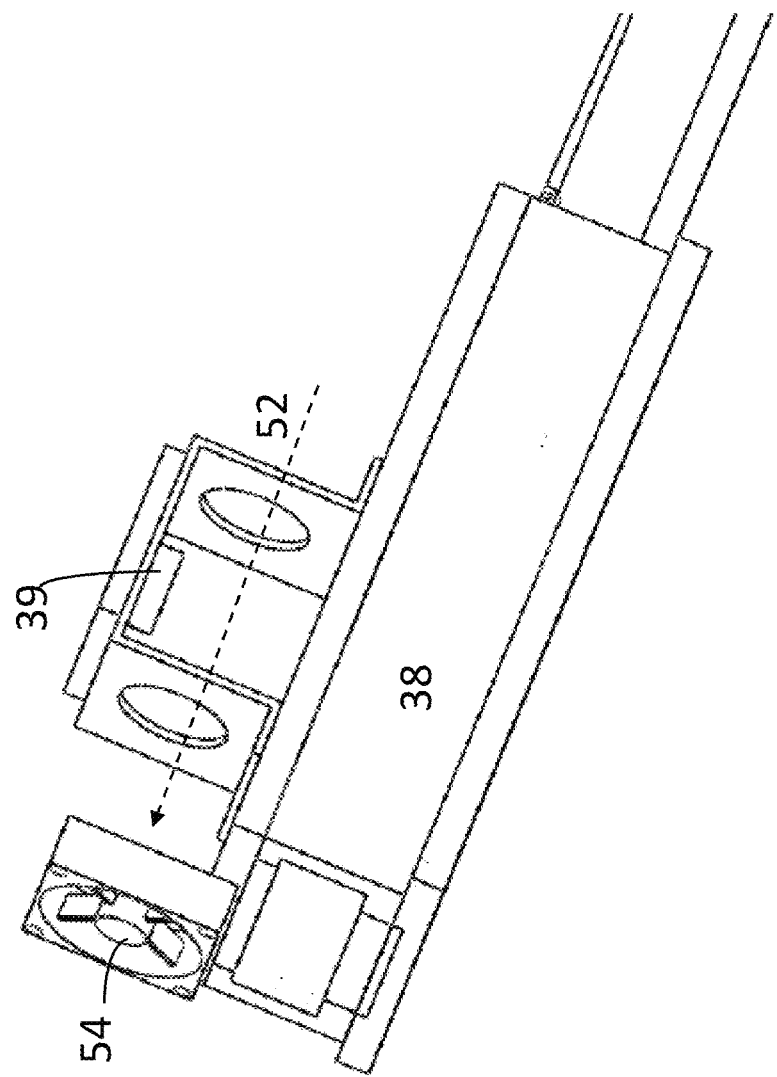
FIG. 5A shows an exemplary perspective view of a camera in a test chamber.

To test a contaminate collection swipe, a user opens the port 30 and places a test swipe such as the swipe of FIG. 1A or 1B into a swipe holder 34. The swipe holder 34 moves along sliding rails 36 when the user closes the port 30 to place the test swipe under a test chamber 38. The test chamber 38 includes a chamber with two openings 52 that face a variable speed fan 54 to draw air across the test swab or test swipe while under test. The test chamber also includes a heating element 56 connected to a PID loop that can warm up the test swab to multiple predetermined temperature settings during test. The test chamber also contains a camera 39 (FIGS. 2B and 5A).

Figure 3:
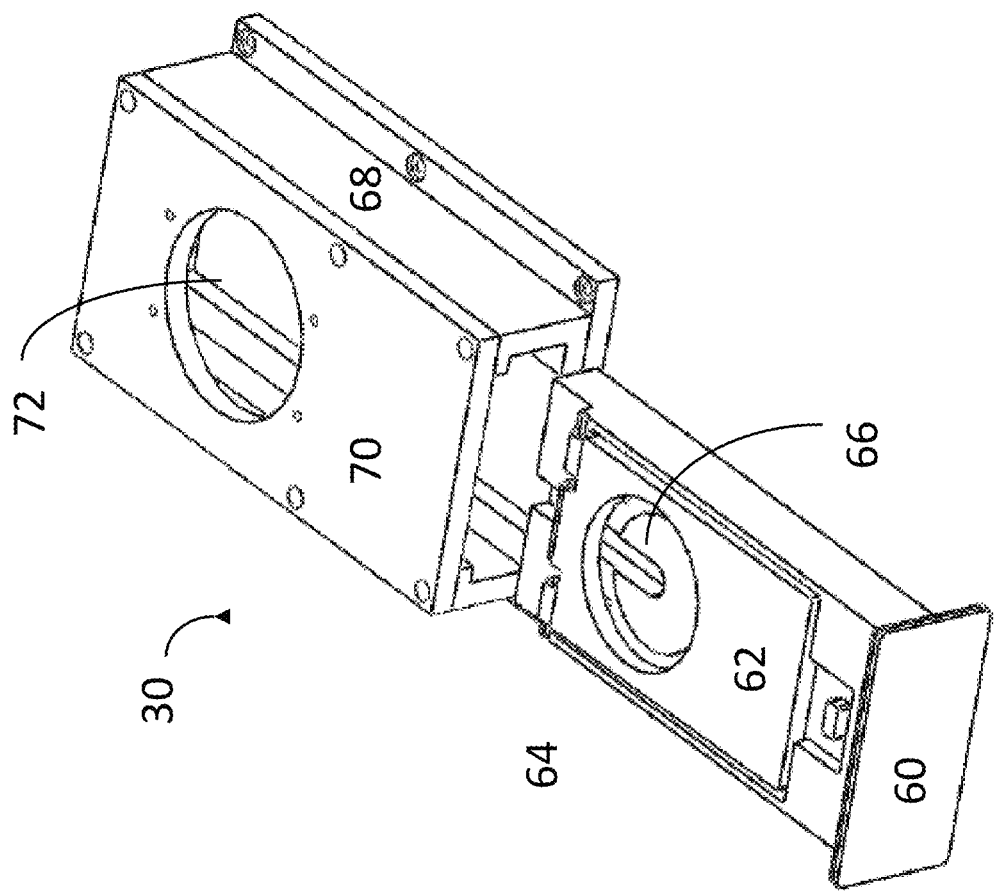
FIG. 3 shows in more details a swipe receiving port.

FIG. 3 shows in more detail port 30 that receives the test swipe in the swipe holder 64. The swipe holder 64 includes a door 60 by which a user can press against to open or close the port 30. The swipe holder 64 also includes an open face press-fit clamp 62 that secures the swipe against a heating element 64 under the swipe upon closure. The swipe holder 64 is attached to rails 66 that slide within rails 68 to enable the swipe holder 64 carrying the test swab of FIG. 1A or 1B to move in and out of the device 10. An enclosure for the swipe holder 64 is formed by positioning a lid 70 with an opening 72 between the sliding rails 68. The opening 72 allows movable tubes from the micro-pumps 46 to dispense test chemicals onto the swipe. The opening 72 also allows a camera 39 (FIG. 5A) to capture images of the test results for automatic real-time analysis of the test. A white-light source such as one or more LEDs are positioned near the camera can be turned on to provide lighting if needed and turned off when not used to conserve power. In one embodiment, the camera output is shown on the display 22 so that the user or operator can visually determine the test result(s) while the automated determination is in progress. The opening 72 also allows a variable speed fan 54 to gently move vapor away from the camera lens to avoid fogging the lens (anti-fogging).

Figure 4A:
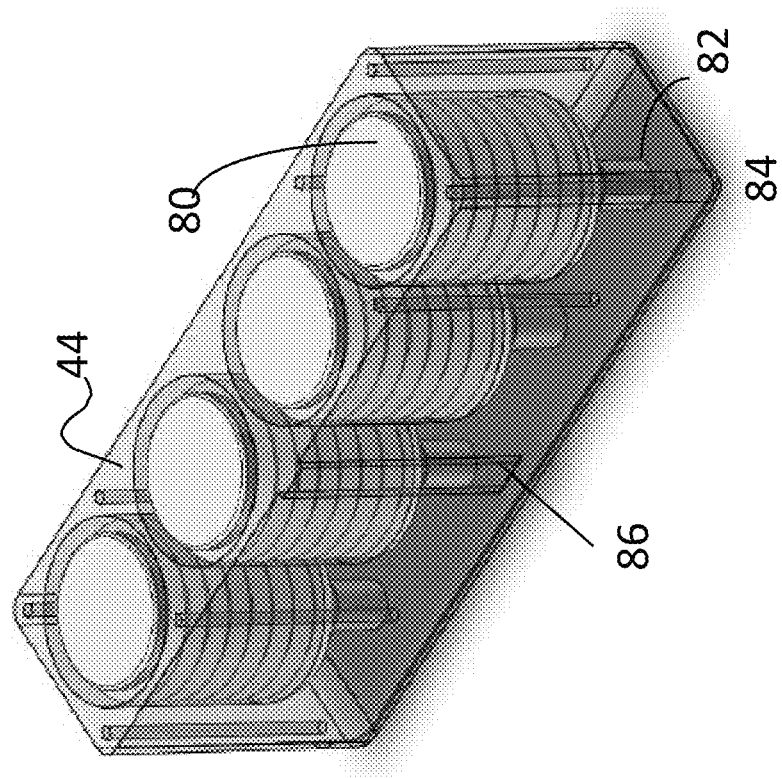
FIG. 4A shows a perspective view of a chemical supply cartridge.

FIG. 4A shows a perspective view of a disposable chemical supply cartridge 44 that can be inserted into the port 40. The disposable cartridge 44 contains one or more reservoirs 80, each having an inlet 82 that can be punctured and is resealable so that the chemical in each reservoir 80 can be accessed by a tip or safety needle 84. The disposable cartridge 44 also has a key 86 cooperating with a recess 87 (FIG. 4B) to ensure that the cartridge 44 can only be inserted in a predetermined orientation.

Figure 4B:
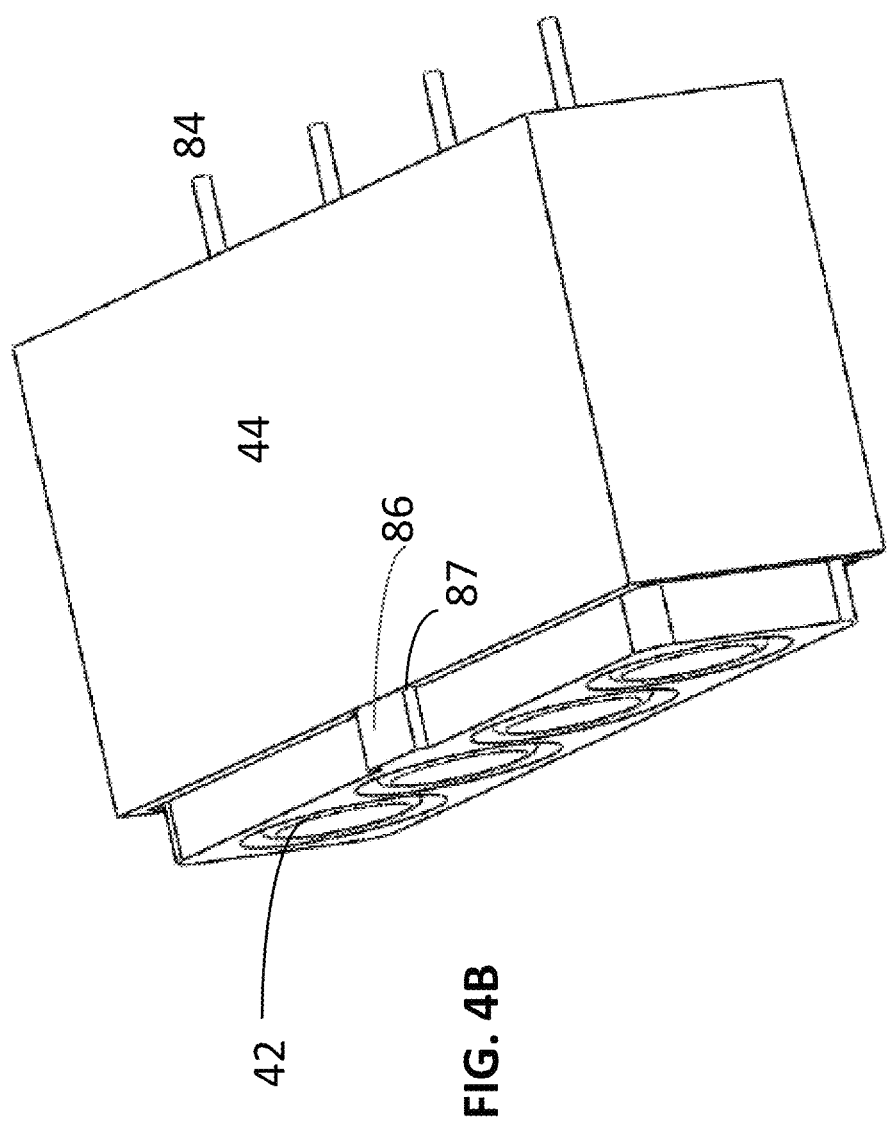
FIG. 4B shows an exemplary perspective top view of a pump assembly.

FIG. 4B shows a pump assembly with the cartridge 44. The needles 84 provide chemicals through short length, narrow gauge tubes (not shown) to their respective inputs 90 at the micro-pumps 46.

FIG. 4C shows an exemplary perspective view of a micro-pump array. As shown therein, a plurality of micro-pumps 46 are provided to pump a series of respective chemicals from the array of reservoirs 80. Each micro-pump has an inlet 90 that is connected to the needles that may or may not include safety tips and that are inserted into each reservoir 80 when the user inserts the cartridge 44 into the device 10. Another set of tubes are connected to the outputs of the micro-pumps 46 to deliver the chemicals in precise volume, sequence and timing as controlled by the processing electronic controller 58.

Figure 5B:
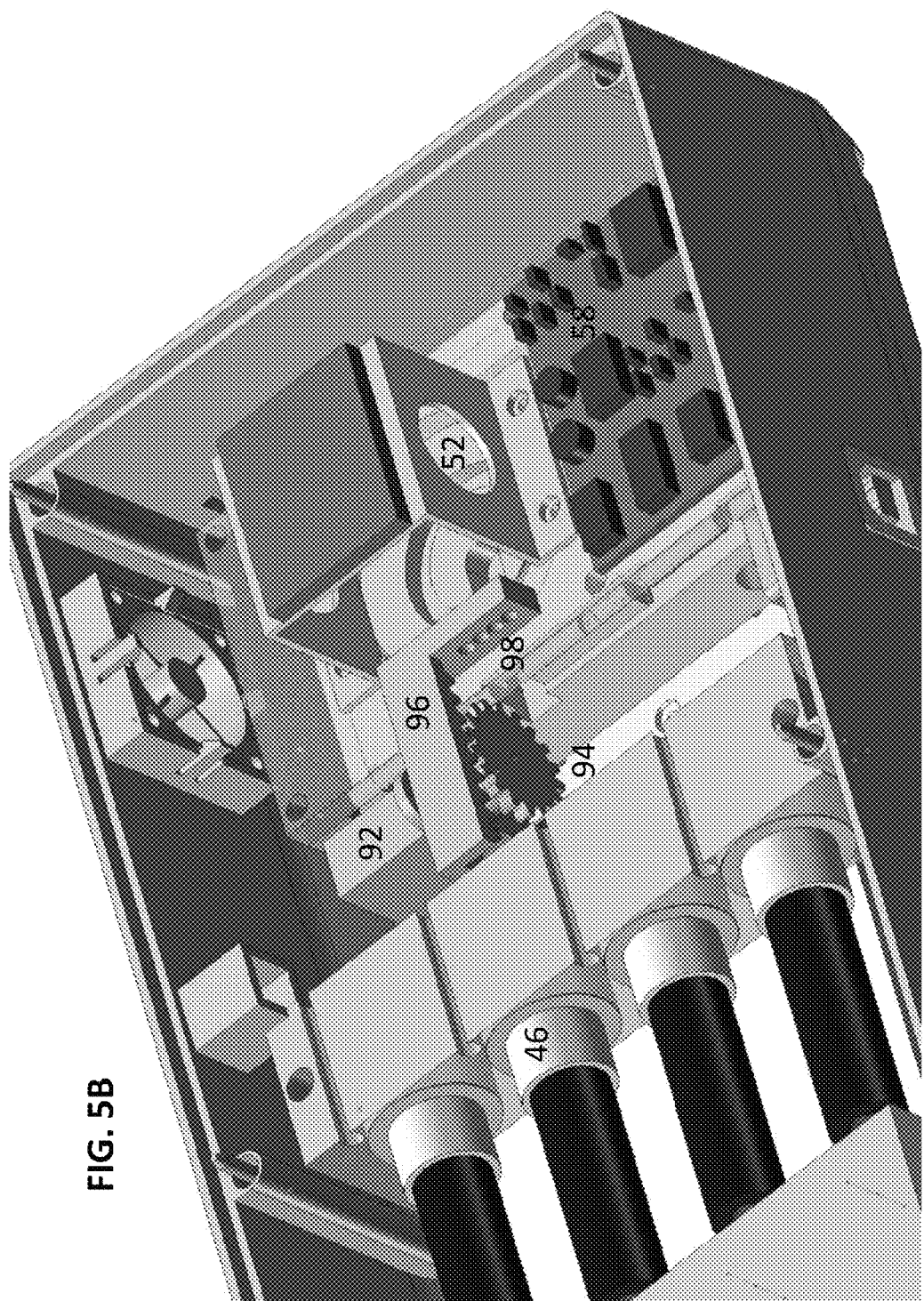
FIG. 5B shows an exemplary perspective view of tubing and camera actuator in the test chamber.

FIGS. 5A and 5B show an exemplary perspective view of a camera 39 in conjunction with the test chamber 38. The chamber 38 includes a motor 92 driving a gear 94. The gear 94 cooperates with a moveable arm 96 that moves test tubing fixture 98 back and forth over the test swab or swipe during testing. The test tubing fixture 96 moves very closely to the swipe for chemical deposit onto the swipe when the device 10 is held in any orientation. The arm 96 includes a plurality of openings that receive a plurality of tubes from the output of the micropumps 46. The arm 96 also moves the fixture 98 out of the way for the camera 39 to capture changes on the test swipe during testing. The camera images are then analyzed, and the result can then be displayed on the display 22. In one embodiment, the camera 39 can capture raw images with 65,536 colors. The camera is protected with an anti-fog feature using the adjustable speed fan 54. The image data can be shown continuously throughout the entire process on a flip-up display 22 with high fidelity. In one embodiment, the system provides a software JPEG (or alternatively bitmap) encoder and decoder for storing and viewing previous results and images. The system also includes white light LEDs (not shown) located within the test chamber 38 that provides even, shadow free, and uniform lighting during camera 39's operation with a programmable white light intensity. The LEDs minimize shadows in the camera viewing area.

The swipe holder 34 moves along rugged sliding rails 66 when the user closes the port 30 to place the test swipe of FIG. 1A or 1B under the test chamber 38. The test chamber 38 includes a chamber with two openings 52 that face the fan 54 to draw air across the test swipe while under test. The test chamber also includes a heating element 56 that can warm up the test swipe to a predetermined temperature during test.

Figure 6:
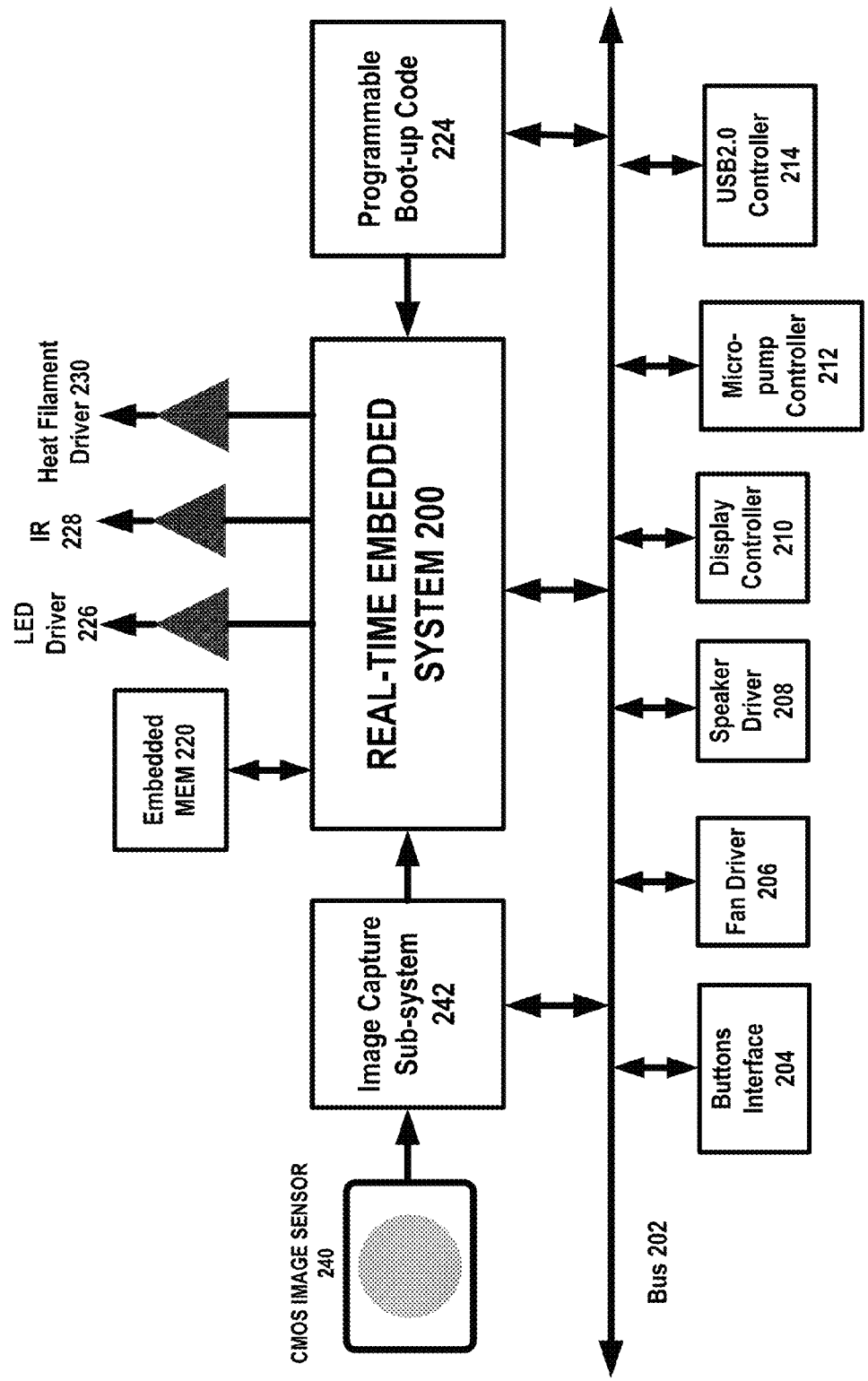
FIG. 6 shows an exemplary block diagram of processing electronics for the system of FIG. 2A.
Figure 7A:
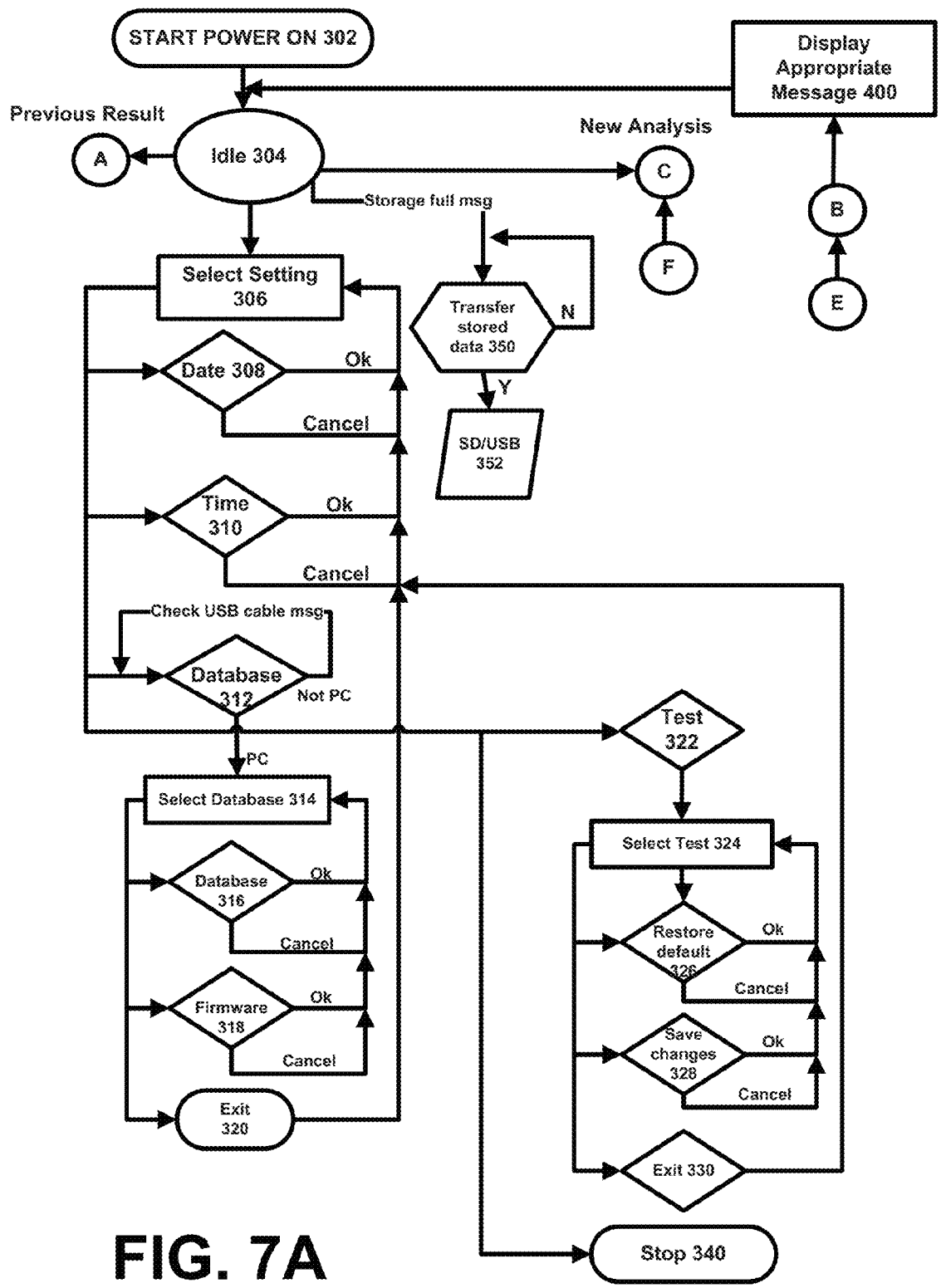
FIGS. 7A-7D show an exemplary operational flow chart executed by the system of FIG. 2A.
Figure 7B:
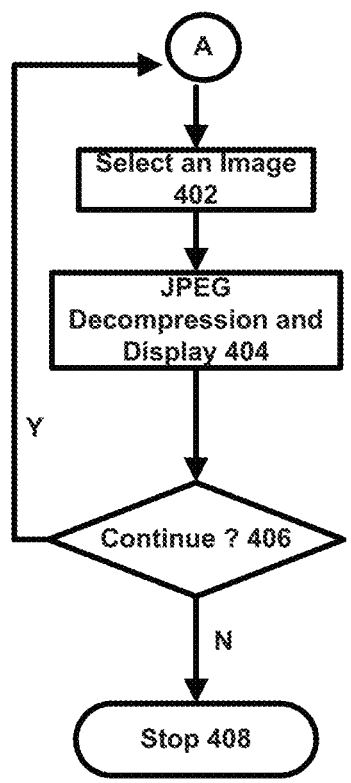
Figure 7C:
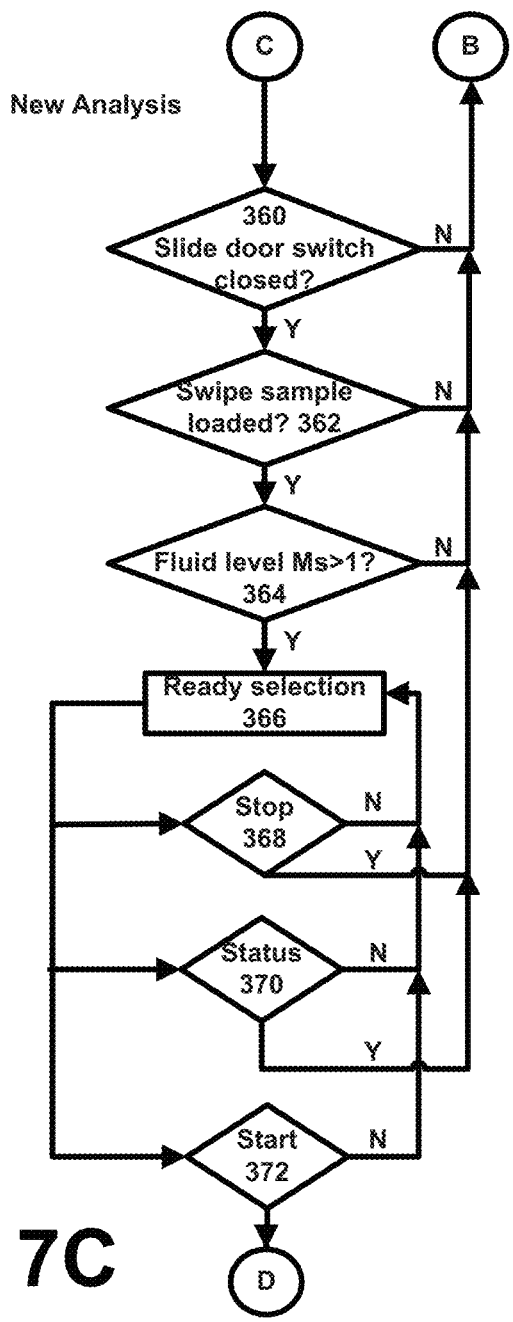
Figure 7D:
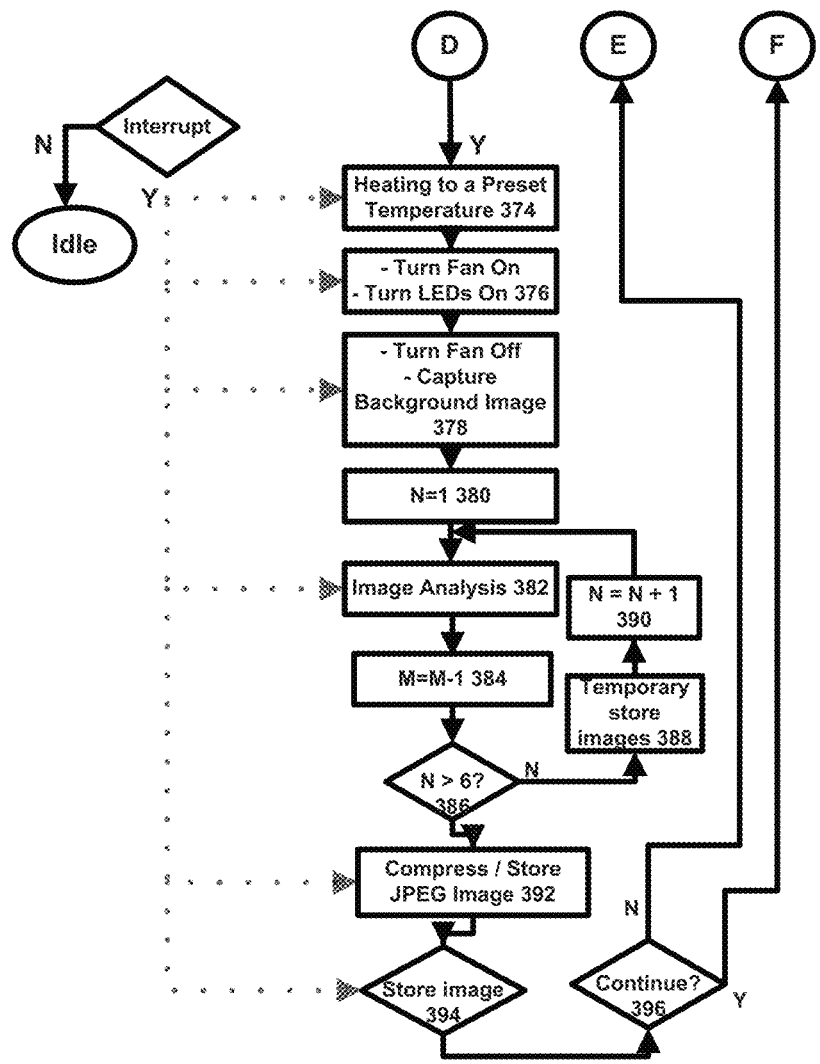

FIG. 6 shows an exemplary block diagram of processing electronics for the system of FIG. 2A. A processor 200 controls all tasks done by the system. The processor 200 communicates over a bus 202 to various devices, including buttons interface 204, fan driver 206, speaker driver 208, display controller 210, micro-pump driver 212, and USB controller 214. The processor 200 also communicates with embedded memory 220 and a programmable ROM 224 that contains boot code as well as application code. The processor 200 also drives buffers 226, 228 and 230 which controls the LED(s), infrared sensor that informs the operator if a swipe has been loaded into the test chamber 38, and heat filament, respectively. The infrared sensor is positioned under the swipe and acts as a proximity sensor to detect the presence or absence of a swipe by the amount of light reflected back. The processor 200 or controller actuates the motor to drive a solution delivery manifold to the center of the swipe and in close proximity to the swipe to dispense the solution without dripping, regardless orientation. The controller can monitor fluid levels within each reservoir contained in the disposable cartridge. This is done by decrementing available volume each time the pump is actuated and when the count reaches a low threshold, the controller can indicate that the reservoir is out of chemical.

The system is powered by a 12-volt DC source, which can be generated from an AC/DC converter, a car outlet or from eight 1.5-volt batteries in series. The highest prioritized energy source is from an AC/DC converter followed by the one from a car outlet, then the energy from batteries. The 12-volt DC power source will supply current to the heater and the pump. It is also connected to the low drop voltage regulator to generate different voltage levels such as 5 V, 2.8 V and 3.3 V, which are necessary for the processor and for other peripherals as well.

One example of the of a sequence involving chemistry time, temperature ramp rates and hold times to optimize each of the results for explosives, drugs, or other threat chemicals within a chemical reaction sequence. The system always adjusts the start temperature prior to running a particular sequence to a predetermined temperature value. An example of this may be 35° C. whereby the swipe retaining a wet or dry sample is adequately held and in intimate contact with the elements of the swipe holder. Not mentioned in this section are the specific parameter controls for fan speed, LED lighting, pumping increments, GUI, camera, speaker, or display.

The background image of the swipe at this temperature is taken so as to subtract out any colors that may be present on the swipe prior to analysis. A selected chemical reactant from one of the reservoirs is then pumped onto the swipe in a non-drip fashion and in a volume of 20-30 µL, most favorable being 25 µL. The system takes second image of the chemically reacted sample on the swipe and immediately processes this image from subtracted background for color indicating peroxides. The second image then becomes the new background image whether peroxides are present or not for the next analyte sought hexamethylene triperoxide diamine HMTD.

Further reacting sample material on the swipe, the heater element begins rapidly heating only the sample area on the swipe with temperature setting ramp rates of 10-20° C. per minute to 115° C., most favorable being 15° C. per minute. During the ramp, a third image is taken between 5-15 seconds, 12 seconds being most favorable, to analyze for color indicating HMTD. The system takes third image of the chemically reacted sample on the swipe and immediately processes this image from second background for presence of HMTD. Once the heater element reaches 115° C., it then holds a for 20-40 seconds, 30 seconds being most favorable. The third image then becomes the new background image whether HMTD was present or not for the next analyte sought triacetone triperoxide TATP.

During the hold time, a fourth image is taken of the chemically reacted sample on the swipe at 25 to 30 seconds, 28 seconds being most favorable, and immediately processes this image from third background for presence of the color indicating TATP. The fourth image then becomes the new background image whether TATP was present or not for the next analyte sought chlorates.

During the same hold time, a fifth image is taken of the chemically reacted sample on the swipe at 25 to 35 seconds, 30 seconds being most favorable, and immediately processes this image from fourth background for presence of the color indicating chlorates. The fifth image then becomes the new background image whether chlorates were present or not for the next analyte sought TNT.

The heater element begins rapidly heating only the sample area on the swipe with temperature setting ramp rates of 10-20° C. per minute to 140° C., most favorable being 15° C. per minute. Simultaneously, a second selected chemical reactant from one of the reservoirs is then pumped onto the swipe in a non-drip fashion and in a volume of 20-30 µL, most favorable being 25 µL. Once the heater element reaches 140° C., it then holds for 10-20 seconds, 10 seconds being most favorable. During the second temperature ramp, a sixth image is taken between 5-15 seconds, 8 seconds being most favorable, to analyze for color indicating TNT. The sixth image then becomes the new background image whether TNT was present or not for the next analytes sought all high explosives.

The heater element begins rapidly heating only the sample area on the swipe with temperature setting ramp rates of 10-20° C. per minute to 155° C., most favorable being 15° C. per minute. Simultaneously, a third selected chemical reactant from one of the reservoirs is then pumped onto the swipe in a non-drip fashion and in a volume of 20-30 µL, most favorable being 25 µL. Once the heater element reaches 155° C., it then holds for 10-20 seconds, 20 seconds being most favorable. During the third temperature ramp, a seventh image is taken between 5-15 seconds, 5 seconds being most favorable, to analyze for colors indicating all high explosives. The seventh image then becomes the new background image whether high explosives were present or not for the next analytes sought all nitrates.

The heater element continues to hold at 155° C. and from 10-20 seconds, an eighth image is taken between 10-20 seconds, 15 seconds being most favorable, to analyze for colors indicating all nitrates. The heater element immediately cools down for the next sample run.

Another example of a single test involving chemistry time, and temperature settings and hold times to optimize results for a chemical reaction involves depositing one or more of the chemical reactants from their respective reservoirs onto the swipe in a non-drip fashion. This is to impart a single spot test or multiple spot tests for a single drug or drugs, a single explosive or explosives, or other threat chemicals at ambient or preset temperature conditions that results in a single color or an array of colors unique to that material under the temperature settings and reagents applied.

In one embodiment as a Portable Explosive Trace Detector (PETD), the system of FIG. 6 significantly enhances the detection of the explosive materials as well as speeding up the screening and detecting procedures at security checkpoints. First, the PETD automatically pumps a series of chemical solution agents into the swiped sample and heats up to specific temperature to accelerate the chemical reactions. Second, an internal CMOS camera captures the chemical reaction images at its highest resolution, raw data for better image analysis. Third it then sends these raw images data to the LCD (Liquid Crystal Display) screen for the purpose of observation. Moreover, the JPEG codec is capable storing and replaying image functions. The LCD screen provides a high quality image for human viewing. In another embodiment, in place of JPEG, a bitmap image or an MPEG video or any suitable imaging storage format can be used. The LCD can analyze the image to identify explosive materials based on the provided chemical reaction database. Last but not least, the PC interfaces can be used to update software and firmware as well as to backup the data.

In one implementation, to start the analysis process, the system turns the micro-pump(s) N (i.e., N=1, 2, 3 . . . or a combination thereof) to disperse the chemical solution into the Swiped Sample. The pumping rate is set to 2 Hz. After dispersing chemical solution, the system starts heating the sample to excite the chemical reactions under controlled vapor, time, temperature, and chemical volume conditions specific to a particular analyte or group of analytes. A current of about one ampere is applied to heat up the heating filament. During the heating process, the fluctuation of the temperature is controlled by a feedback circuit with a thermistor.

When the temperature of the sample swipe reaches a predefined value, the system turns the heater off, the white light LED on and the fan on. The speed of the fan is adjustable using pulse width modulation control in one embodiment.

Before commanding the camera's CMOS image sensor to capture an image, the system waits for the chemical reaction to complete for around 1 ms. The captured image is then displayed on the LCD.

The system creates a result image by subtracting the captured image from the background one. Then the result image is compared with the color patterns in the lookup table stored in the system. If the results image matches some color pattern, the result probability will be displayed and an optional audible alarm is given or not. Otherwise, an appropriate message is displayed on the LCD.

During the process of writing to the memory, (e.g., saving results or updating database), the system is able to detect the memory capacity and give the user a warning of full memory. In such a case, the user needs to clear the memory by deleting certain files before commanding the system to continue its work.

In one embodiment, the system executes a prime pump procedure to clear up air and chemical bubbles in the tubes of minimized length and diameter once the system has been idled for more than 12 hours. If the system has not been used for the past 12 hours then the system prompts the user to place an empty swipe sample into a clamp holder. Once a swipe sample is secured on the clamp holder, the system prompts user to do the prime pump procedure by pumping chemical solutions onto swipe sample. During the prime pumps, the camera captures the image from the swipe and displays it on the LCD screen. During the prime pumps, no heat is applied to the swipe.

In one embodiment, in the main menu, user can see the date, the time and current status of the system. The system can generate a warning alarm once battery, chemical level and memory reach their minimal levels. The menu also contains three (3) software programmable buttons, namely New Analysis, Previous Results, and Settings. User can interact with these soft buttons by using the five hard buttons. The New Analysis option is highlighted as default. The usage of these soft buttons is as follows:

New Analysis: allows user to perform a new test.
Previous Results: allows user to trace back the data tested in the past.
Settings: allows user to set parameters such as date, time, to test the system reliability, or to connect to PC for firmware and/or database update.

The user can see the images taken by the camera. The system status is also displayed. In addition, three (3) soft buttons (Start, Stop, and Status) are provided. The Start option is highlighted as default.

FIGS. 7A-7D (collectively FIG. 7) show an exemplary operational flow chart executed by the system of FIG. 2A. When the system is turned on by pressing the Start Power On button, it will stay in IDLE state 304. In this state, the system waits for user commands. By default, both the camera lighting LEDs and the fan are turned off to save power. The system sends an appropriate message alarm to operator once chemical, battery, and memory reach their minimal level. User may command the system to perform a new test by selecting New Analysis, to view previous results and images by selecting Previous Results, or to update the firmware and/or database.

When the option of performing a new test is selected, the system checks whether the Slide Door Switch closed or not (360) via an infrared sensor (362). If the door is not closed, it will display a warning message (400) and return to IDLE state 304. Otherwise, it looks for a loaded swiped sample using the infrared sensor (362). The presence of the sample allows the system to move to the next state, where it checks for the fluid levels of the three reservoirs to ensure that the fluids are enough for the entire test process (364). The amount of fluid is determined by the number of dispensing (i.e., a full bottle is enough for a predetermined number of dispenses and the number is decremented during each dispensing).

Before continuing, the system checks the temperature of the filament if it is equal to 35° C. in one embodiment. Otherwise, it will have to heat the filament until the temperature of the filament reaches 35° C. (374). At this temperature, the user is allowed to choose different options. If the user presses the Stop button (368), the system will stop the work and return to the IDLE state. If the user chooses the Status button (370), the system will temporarily display its current task to turn the system status on/off. After that it returns and continues the previous work. When the user presses Start button (372), the system turns the Fan on to blow the fog or vapor away from the camera, turns the LEDs on, turns the fan 39 to a low speed and takes a background image using the camera (378). Then, the system will select a particular micropump N=1 or a series of micro-pumps (N=1, 2, 3 . . . or a combination thereof) and start analyzing the sample based on the image analysis process (380-386). Once the New Analysis operation is in process, it takes a number of different tests (in one embodiment seven tests) non-stop and summarizes the test results after the last test has completed. The image results are saved automatically as a group by a time date stamp and can be further sorted by positive or negative results for ease of viewing recall (392-394). Different audible sounds can be played at the end of each test to catch the operator's attention. The image result is obtained by subtracting the current image from its initial background image. After finishing this analysis, the system asks user if he/she wants to review the test summary or else return to the main menu.

When the option of viewing previous results is selected, the user can select his/her desired filename and presses Display button to command the system to decompress and display the image and/or other necessary information (402-408).

When the option of updating date, time, database and/or firmware is selected (306), the system shows a menu to allow the user to choose different options such as update date, time, or upgrade the firmware, or test the reliability of the system. For example, when the user presses the date button (308), the system allows the user to change the date via the buttons of the system. After the date is confirmed to be changed, the system will store the change in its memory and return to the previous menu to allow the user to choose other options. The change of the time functions in the same manner as the change of the date (310).

In case the user wants to update the database by pressing Database button (316), the system communicates with the PC in order to set up a channel for data transfer (312). Upon a successful connection the user can update database and/or firmware. After the firmware or database is updated, the user presses the Ok button to return to the main menu. When the system connects to the PC unsuccessfully, it warns the user to check the connection (316).

When the user wants to test the reliability of the system, the user can press the Test button (322). As soon as this button is pressed, the user can test different system parameters. He/she can save the changed parameter or restore default parameter. When the user presses Exit button, system returns to the main menu.

By having all components under program control and by arranging for a known input to the system such as a controlled injection of target material, the system can perform self-calibration and self-diagnostic. The function of this program is to calibrate the entire system and determine and store the required time, and temperature parameter, among others. If these parameters are not within specified limits for any reason, the program can alert the user. Guided by a service program the user response can range from immediate shutdown to scheduling service at a later date, to simply noting the circumstances.

Figure 8:
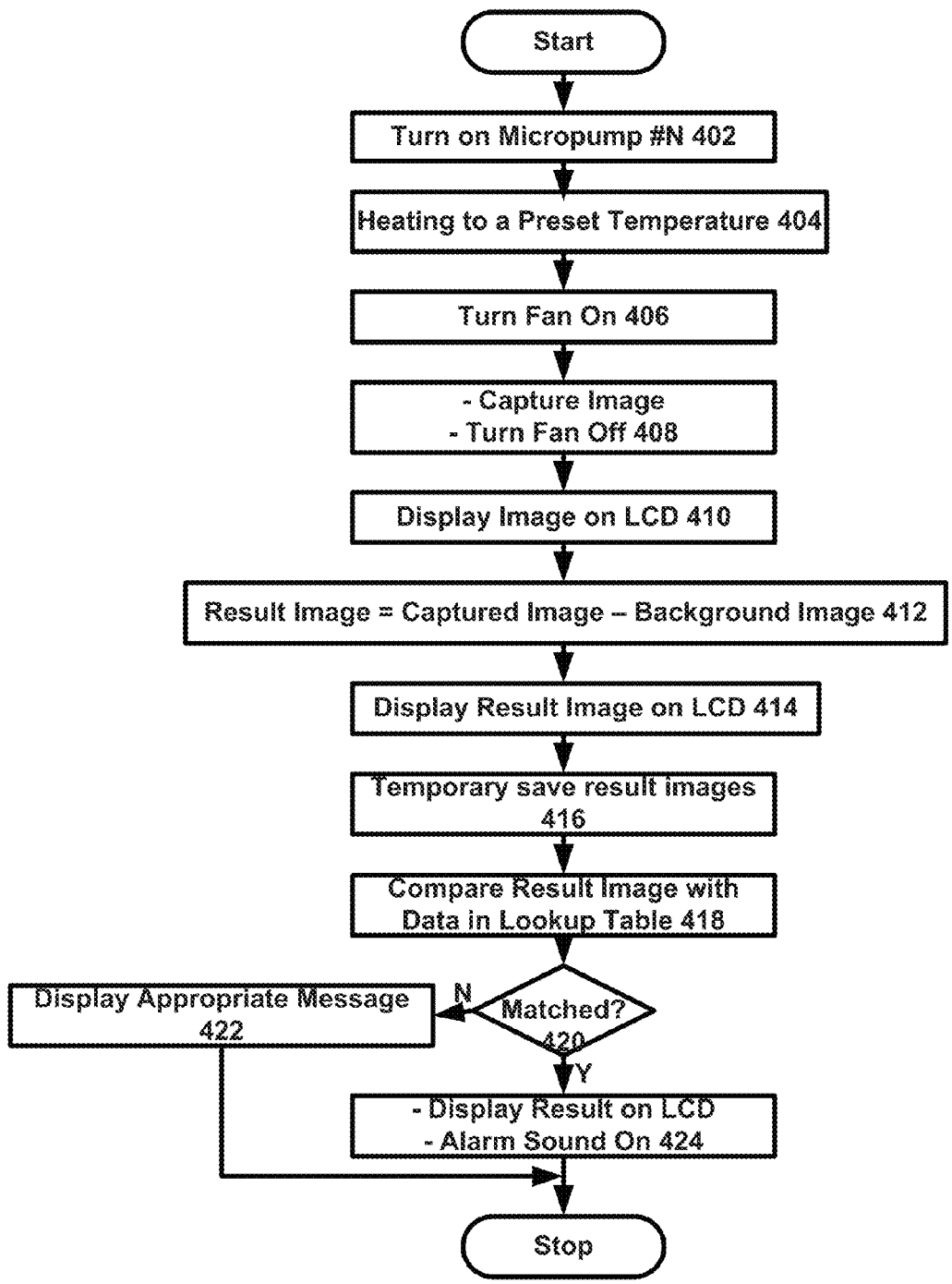
FIG. 8 shows an exemplary image analysis process executed by the processor of FIG. 5 to detect chemical agents automatically.

FIG. 8 shows an exemplary image analysis process executed by the real-time embedded system processor 200 to detect chemical agents automatically. To start the analysis process, the system turns the micro-pump(s) N (i.e., N=1, 2, 3 . . . or a combination thereof) to disperse the chemical solution into the swiped sample. The pumping rate is set to 0.250 Hz. After dispersing chemical solution, the system starts heating the sample to excite the chemical reactions. A current of about 1 Ampere is required to heat up the heater filament. When the temperature of the sample reaches a predefined value, the system turns the heater off, the LED and the fan on. In one embodiment, before commanding the CMOS image sensor to capture an image, the system waits for the chemical reaction under optimized: time, temperature, volume dispensed, and vapor to complete for around 1 millisec. The captured image is then displayed on the LCD. The system creates a result image by subtracting the captured image from the background one. Then the result image is compared with the color patterns in the lookup table stored in the memory. If the results image matches some pattern, the result will be displayed and an audible alarm is given. Otherwise, an appropriate message is displayed on the LCD.

Due to the automated, reproducible analysis, the system provides an objective indication of potential threats with more accurate, un-biased results at night, high humidity, or bad weather conditions, and therefore, more convenient.

The invention may be implemented in hardware, firmware or software, or a combination of the three. Preferably the invention is implemented in a computer program executed on a programmable computer having a processor, a data storage system, volatile and non-volatile memory and/or storage elements, at least one input device and at least one output device.

By way of example, a block diagram of a computer to support the system is discussed next. The computer preferably includes a processor, random access memory (RAM), a program memory (preferably a writable read-only memory (ROM) such as a flash ROM) and an input/output (I/O) controller coupled by a CPU bus. The computer may optionally include a hard drive controller which is coupled to a hard disk and CPU bus. Hard disk may be used for storing application programs, such as the present invention, and data. Alternatively, application programs may be stored in RAM or ROM. I/O controller is coupled by means of an I/O bus to an I/O interface. I/O interface receives and transmits data in analog or digital form over communication links such as a serial link, local area network, wireless link, and parallel link. Optionally, a display, a keyboard and a pointing device (mouse) may also be connected to I/O bus. Alternatively, separate connections (separate buses) may be used for I/O interface, display, keyboard and pointing device. Programmable processing system may be preprogrammed or it may be programmed (and reprogrammed) by downloading a program from another source (e.g., a floppy disk, CD-ROM, or another computer).

Each computer program is tangibly stored in a machine-readable, removable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

The invention has been described herein in considerable detail in order to comply with the patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A method to analyze a swiped sample to identify a chemical composition, comprising:
   applying one or more test chemicals to a pad with one or more processor controlled dispensers;
   adjusting the temperature of the pad to a predetermined temperature range at a rate of 10-20° C. per minute to 140° C. using a processor controlled heater;
   pumping a selected chemical reactant from one of the reservoirs to the pad in a volume of 20-30 µL,
   upon contact with one or more chemicals in concert with heating and time profiles, displaying a sequence of a plurality of color reactions indicative of one from multiple analytes, including explosives, drugs, or household chemicals;
   capturing using a camera an image of the pad after the application of chemical at the predetermined temperature range;
   capturing images between 5-15 seconds and storing as a background image;
   subtracting the background image from the image for generating a difference value from the two images; and
   searching a known database to identify the substance.

2. The method of claim 1, comprising detecting an explosive compound.

3. The method of claim 2, wherein each chemical causes the pad to display a color unique to the explosive compound.

4. The method of claim 2, wherein the sequence of chemicals are deposited onto the pad at predetermined times.

5. The method of claim 2, wherein the sequence of chemicals are deposited onto the pad at predetermined temperature range(s).

6. The method of claim 2, wherein the sequence of chemicals are deposited onto the pad at predetermined hold time(s) each at predetermined temperature range(s).

7. The method of claim 2, wherein each chemical deposited under predetermined time and temperature conditions reacts to a specific explosive or class of explosives to yield a specific color or a sequence of colors unique to that explosive.

8. The method of claim 1, wherein the pad comprises a substantially round shape and adapted to receive a sequence of one or more chemicals to detect an explosive compound.

9. The method of claim 1, wherein the pad comprises a substantially four-sided shape.

10. The method of claim 1, comprising detecting one or more drug compounds.

11. The method of claim 10, wherein each chemical causes each pad to display a color unique to the drug compound.

12. The method of claim 10, wherein the sequence of chemicals is deposited onto the pad at predetermined times.

13. The method of claim 10, wherein the sequence of chemicals is deposited onto the pad at predetermined temperature range(s).

14. The method of claim 10, wherein the sequence of chemicals are deposited onto the pad at predetermined hold time(s) each at predetermined temperature range(s).

15. The method of claim 10, wherein each chemical deposited under predetermined time and temperature conditions reacts to a drug compound to yield a specific color unique to that drug compound.

16. The method of claim 1, wherein the pad comprises a substantially four-sided shape and adapted to receive a sequence of one or more chemicals to detect a drug compound.

17. The method of claim 1, wherein the area comprises a plurality of test regions and wherein a plurality of unique chemical solutions deposited on each test region to impart a collective color code of pads unique to a class of drugs.

18. The method of claim 1, wherein the base comprises a dull black color, comprising a pad region having a cloth within a white zone on the base and an ink free border, wherein the one or more pads are positioned in a white zone.

19. The method of claim 1, further comprising:
   clamping the base under a camera and above a heater; and
   sending the images to the a display screen for operator observation.

* * * * *